United States Patent [19]
Murphy-Chutorian et al.

[11] Patent Number: 5,855,577
[45] Date of Patent: Jan. 5, 1999

[54] BOW SHAPED CATHETER

[75] Inventors: Douglas R. Murphy-Chutorian; Jeffrey Giba, both of Sunnyvale; Michael Horzewski, Santa Clara, all of Calif.

[73] Assignee: Eclipse Surgical Technologies, Inc., Sunnyvale, Calif.

[21] Appl. No.: 797,239

[22] Filed: Feb. 7, 1997

Related U.S. Application Data

[63] Continuation-in-part of Ser. No. 714,893, Sep. 7, 1996, Pat. No. 5,755,714.

[51] Int. Cl.$^6$ ..................................................... A61B 17/36
[52] U.S. Cl. ................................................. 606/7; 606/15
[58] Field of Search .................................. 606/7, 13–17, 606/167, 185; 604/281; 607/122

[56] References Cited

U.S. PATENT DOCUMENTS

| | | | |
|---|---|---|---|
| 3,890,977 | 6/1975 | Wilson | 128/418 |
| 4,658,817 | 4/1987 | Hardy | 128/303.1 |
| 4,846,171 | 7/1989 | Kauphusman . | |
| 5,104,393 | 4/1992 | Isner et al. | 606/15 |
| 5,109,830 | 5/1992 | Cho . | |
| 5,255,679 | 10/1993 | Imran | 128/642 |
| 5,380,316 | 1/1995 | Aita et al. | 606/7 |
| 5,389,096 | 2/1995 | Aita et al. | 606/15 |
| 5,465,717 | 11/1995 | Imran et al. | 128/642 |
| 5,575,787 | 11/1996 | Abela et al. . | |
| 5,607,462 | 3/1997 | Imran . | |

FOREIGN PATENT DOCUMENTS

| | | |
|---|---|---|
| 0 515 867 | 12/1992 | European Pat. Off. . |
| WO96/35469 | 11/1996 | WIPO . |

OTHER PUBLICATIONS

Deckelbaum, "Cardiovascular Apps. of Laser Tech.", Lasers in Surgery and Medicine, 15:315–341 (1994).

Frazier et al., "Myocard. Revasc. with Las.", Cullen Cardio. Res. Labs., Tx. Heart Inst., Supp. II C vol. 92, No. 9, II–58–65 (Nov. 1, 1995).

Duering et al. "Structure & Properties of TI–NI Alloys:Nitinol Devices & Comp." In Press. *Titanium Handbook*. ASM.

*Primary Examiner*—Ruth S. Smith
*Attorney, Agent, or Firm*—Ray K. Shahani, Esq.; Ilene Lapidus Janofsky, Esq.

[57] ABSTRACT

A bow shaped, integrated wire catheter apparatus and method of use for access to, and laser or other treatment within, cavities and organs in the human body, the apparatus having a curvilinear shape but flexible enough to assume a generally elongated shape such that the apparatus can be extended through the vasculature in the generally elongated shape and can assume the curvilinear shape when extended into a body cavity or organ, the curvilinear shape serving to securely position the apparatus adjacent a selected surface within the body cavity or organ for laser or other treatment with a laser delivery device or other functional device thereon, the apparatus having a central axis, the apparatus comprising a main catheter shaft having a proximal end and an apex seeking and stabilizing distal end, the main catheter shaft having material of construction or other mechanism or means for causing a portion of the catheter shaft to have a bowed shape adjacent its distal end, the main catheter shaft having at least one hollow lumen extending axially and at least partially therethrough such that a bow shaped portion defines and distinguishes an outer arcuate sidewall for placement in contact with the selected area or areas for laser or other treatment thereon, and an inner arcuate sidewall, at least the outer arcuate sidewall having one or more guide holes disposed thereon for selectively providing laser or other treatment on the selected surface by controllably advancing a laser delivery device or other functional device selectively through the one or more guide holes to the selected surface. The catheter apparatus can be made at least partially of superelastic and/or shape memory materials of construction.

27 Claims, 5 Drawing Sheets

BOW SHAPED CATHETER

RELATED APPLICATIONS

This application is a Continuation-In-Part application of U.S. patent application Ser. No. 08/714,893 filed Sep. 7, 1996, U.S. Pat. No. 5,755,714 the specification, drawings and claims hereby incorporated herein in their entireties.

FIELD OF THE INVENTION

The present invention relates generally to catheters and catheter procedures involving laser energy delivery using fiber optic and other laser delivery systems. More particularly, the invention relates to a bow shaped catheter apparatus with integrated guide wire having a bow shaped shaft with a number of guide holes at its distal end, and at least one lumen extending therethrough for selectively directing the distal end of an optical fiber, other type of laser delivery means or other device through the guide holes on the shaped shaft, particularly adapted for use in laser-assisted transmyocardial revascularization (TMR).

BACKGROUND OF THE INVENTION

In the treatment of heart disease, one method of improving myocardial blood supply is called transmyocardial revascularization (TMR), the creation of channels in the myocardium of the heart. The procedure using needles in a form of surgical "myocardial acupuncture" has been used clinically since the 1960s. Deckelbaum. L. I., Cardiovascular Applications of Laser Technology, *Lasers in Surgery and Medicine* 15:315–341 (1994). The technique relieves ischemia by allowing blood to pass from the ventricle through the channels either directly into other vessels communicating with the channels or into myocardial sinusoids which connect to the myocardial microcirculation.

In the reptilian heart, perfusion occurs via communicating channels between the left ventricle and the coronary arteries. Frazier, O. H., Myocardial Revascularization with Laser—Preliminary Findings, *Circulation,* 1995; 92 [suppl II]:II-58-II-65. There is evidence of these communicating channels in the developing human embryo. In the human heart, myocardial microanatomy involves the presence of myocardial sinusoids. These sinusoidal communications vary in size and structure, but represent a network of direct arterial-luminal, arterial-arterial, arterial-venous, and venous-luminal connections. This vascular mesh forms an important source of myocardial blood supply in reptiles but its role in humans is poorly understood.

Numerous surgical TMR studies have been performed, including early studies using needles to perform myocardial acupuncture, or boring, to mechanically displace and/or remove tissue. Such studies have involved surgically exposing the heart and sequentially inserting needles to form a number of channels through the epicardium, myocardium, and endocardium to allow blood from the ventricle to perfuse the channels. The early studies using needles showed that the newly created channels were subject to acute thrombosis followed by organization and fibrosis of clots resulting in channel closure. Interest in TMR using needles waned with the knowledge that such channels did not remain open. However, interest in TMR procedures has recurred with the advent of medical lasers used to create TMR channels. Histological evidence of patent, endothelium-lined tracts within laser-created channels shows that the lumen of laser channels can become hemocompatible and resists occlusion. A thin zone of charring occurs on the periphery of the laser-created channels through the well-known thermal effects of optical radiation on cardiovascular tissue. Additionally, recent histological evidence shows probable new vessel formation adjacent collagen occluded transmyocardial channels, thereby suggesting benefits from TMR with or without the formation of channels which remain patent.

Surgical TMR procedures using laser energy have been described in the prior art. U.S. Pat. No. 4,658,817 issued Apr. 21, 1987 to Hardy teaches a method and apparatus for surgical TMR using a $CO_2$ laser connected to an articulated arm having a handpiece attached thereto. The handpiece emits laser energy from a single aperture and is moved around the surface of the heart to create the desired number of channels. U.S. Pat. No. 5,380,316 issued Jan. 10, 1995 to Aita et al. purports to teach the use of a flexible lasing apparatus which is inserted into the open chest cavity in a surgical procedure. A lens at the distal end of the flexible apparatus is used to focus laser energy, and the apparatus is moved about the surface of the heart to create the desired number of channels.

The foregoing discussion relates to surgical procedures, i.e. procedures which access the heart surgically, either via open heart surgery, or perhaps by minimally invasive surgical (MIS) methods if the design and size of the distal ends of the hand pieces are suitable for use in an MIS site. However, since TMR most often involves creating channels through the endocardium into the lower left chamber of the heart, it is desirable to create TMR channels in a percutaneous procedure, i.e. by extending a catheter apparatus through the vasculature into the ventricle and creating the channels through endocardial surfaces and into myocardium. Performing such percutaneous TMR is desirable for a number of reasons. Percutaneous catheter procedures are typically less traumatic to the patient compared to surgical procedures. Adhesions between the pericardial sac and epicardium are eliminated. Percutaneous TMR with a catheter apparatus also offers an alternative solution to persons who are not candidates for surgical procedures.

Because TMR procedures generally involve creating a plurality of channels within the myocardium, performing the procedure percutaneously requires the ability to steer a catheter apparatus through the vasculature and maneuver the apparatus within the ventricle of the beating heart as rapidly as possible to create the channels without subjecting the heart to the undue stress of a lengthy procedure. Additionally, the ability to control and stabilize the catheter apparatus against the beating heart wall while creating channels with a laser is desirable for percutaneous procedures to ensure creation of channels as desired and to ensure that the laser is fired only within the myocardial tissue. TMR channels should be spaced and grouped appropriately to achieve the desired result without weakening or rupturing the heart muscle.

The early myocardial acupuncture procedures were not performed percutaneously. The Hardy $CO_2$ laser delivery system described above is rigid, relatively large, and not adaptable for percutaneous use. The Aita '316 patent does not suggest a method for percutaneous use of the single aperture, laser delivery device described therein for surgical use.

U.S. Pat. No. 5,389,096 issued Feb. 14, 1995 to Aita et al. purports to teach one method of percutaneous TMR using an elongated flexible lasing apparatus with control lines and a focusing lens structure at the distal tip. The method describes the use of pressure to attempt to stabilize the apparatus against the wall of the heart. The '096 apparatus requires movement and restabilization of the apparatus prior to the creation of each channel. Neither of these patents, nor any other prior art, describes or suggests creation of more than one TMR channels without the necessity for repositioning the catheter device.

Several prior art patents describe the use of catheters within the ventricle for percutaneous treatment of ventricular tachycardia. Such devices have a means to locate an arrhythmia site and ablate the site, at or just below the ventricle surface, using an electrode device or laser energy. U.S. Pat. No. 5,104,393 issued Apr. 14, 1992 to Isner teaches a catheter apparatus having a guiding Y-shaped sheath and guide catheter assembly for introducing an optical fiber into the ventricle. Positioning is described to enable a single burst of laser energy from a single aperture to ablate the site. However, positioning or specific steering means sufficient to create one or more TMR channels is not described or suggested.

U.S. Pat. Nos. 5,255,679 issued Oct. 26, 1993 and 5,465,717 issued Nov. 14, 1995 to, respectively, Imran and Imran et al., disclose non-laser, basket-shaped catheter apparatus for mapping and/or ablation of arrhythmia sites within the ventricle. A pull wire is used to expand the basket portion within the ventricle, and a plurality of electrodes on the arms of the basket are used for ablation. The basket device is designed to place the electrodes on the ventricle wall. Although the device allows for a fairly extensive mapping procedure without repositioning, no positioning means is provided for a laser delivery system to allow creation of TMR channels.

The use of superelastic and/or shape memory materials is widely known. *Structure and Properties of Ti-NI Alloys: Nitinol Devices & Components,* Duerig et al., In Press, Titanium Handbook, ASM (1994) In general, binary compositions of Nickel (Ni) and Titanium (Ti), yield alloys with shape memory and superelastic properties. These alloys are commonly referred to as Ni-Ti, nitinol, and other industry names. Their precise physical and other properties of interest are extremely sensitive to the precise Ni/Ti ratio used. Generally, alloys with 49.0 to 50.7 atomic % of Ti are commercially available, with superelastic alloys in the range of 49.0 to 49.4%, and shape memory alloys in the range of 49.7 to 50.7%. Due to a rapid decrease in the ductility of the material, binary alloys with less than 49.4 at. % Ti are generally unstable. In general, these types of materials exhibit hysteresis, defined as a phenomenon exhibited by a system whose state depends on its previous history, and illustrated diagrammatically by the familiar upper and lower curves which meet at the ends and define an area under the curves. In the case of solid materials undergoing elastic hysteresis (as opposed to magnetic or electrical hysteresis), the curves are related to stress necessary to cause deformation or otherwise overcome existing stress in pre-stressed materials.

All properties of these materials change significantly as their respective "phase transformation temperatures" are approached. In general, at lower temperatures, these alloys will exist in a martensite state characterized as hard and easily deformed. However, in austenite, the high temperature phase, the alloys have a much higher yield and flow stresses. The addition of small amounts of third elements in the alloy can also have very significant effects on performance of the materials. Elements including but not limited to oxygen (O), nitrogen (N), iron (Fe), aluminum (Al), chromium (Cr), cobalt (Co) vanadium (V), zirconium (Zr) and copper (Cu), though having various effects on the Ni-Ti matrix, can have the tendency to increase strength, increase stiffness, control hysteresis and/or decrease or increase phase transition temperatures.

Ni-Ti products are commonly used in the form of cold drawn wire or as barstock. Tubing is also available. The toxicity of the alloy or the solubility or other compatibility with the biological environment in which catheter equipment is used is an important consideration. The alloys are commonly used in a cold worked and partially annealed condition. The partial anneal does not recrystallize the material but does bring about the onset of recovery processes. The extent of the post-cold worked recovery depends upon many aspects of the application, such as the desired stiffness, fatigue life, ductility, recovery stress, etc. Ni-Ti is difficult to join since most mating materials cannot tolerate the large strains experienced by Ni-Ti. Most connections will rely on crimped bonds. Although Ni-Ti can be brazed or welded to itself with relative ease, such as by resistance and with TIG methods, brazing or welding to other materials is difficult though proprietary methods do exist and are practiced in large volumes, for example in the production of eyeglass frames.

For the purposes of this disclosure, a distinction between superelastic materials and shape memory materials is made. Superelasticity refers to the highly exaggerated elasticity, or springback, observed in many Ni-Ti alloys deformed at a specific temperature. The function of the material in many of such cases is to store mechanical energy. Though limited to a rather small temperature range, these alloys can deliver over 15 times the elastic motion of a spring steel, i.e., withstand a force up to 15 times greater without permanent deformation. Shape memory materials will refer to those materials which can be deformed, but which will freely recover their original shapes during heating, often utilizing electrical resistivity, or which will develop a large recovery stress when recovery is prevented. Applications of these shape materials include various types of fasteners and tube/pipe connectors. It will be understood that a significant difference or distinction between such superelastic and shape memory materials is the phase or transition temperature below which they may be deformable and above which they will return to their original, preformed shape. With regard to the present invention, it will be understood that the transition temperature of materials must, in general, be somewhat above body temperature by at least 10°–12° C.

U.S. Pat. No. 3,890,977 issued Jun. 24, 1975 to Wilson teaches kinetic memory electrodes, catheters and cannulae. These devices incorporate a material, such as a Ni-Ti alloy, having heat-activated mechanical memory properties. The device is formed into an operative shape at a high temperature. Then, at a low temperature below its transitional temperature, it is reformed into a shape for ease of insertion into a guide catheter or the like or otherwise through a portion of a patient's vasculature or other body lumen. When located in the organ or other desired region, those portions of the device constructed using such shape memory materials are heated to above their transitional temperatures, using electrically resistive elements, thereby returning the catheter to its original annealed anchoring or proper locating shape. An important drawback of the Wilson apparatus is that heat must be applied to the catheter tip. Complicated construction and electrical power distribution must be considered.

As can be seen from a description of the prior art above, percutaneous TMR catheters are virtually unknown with the exception of the catheter briefly described in the '096 Aita patent. There is a need in the art for a percutaneous TMR catheter shaped to correspond to the contours of the ventricle, having means for easily positioning and repositioning the catheter against the ventricle wall, and having a port for a laser delivery means to enable rapid creation of a plurality of appropriately grouped and spaced TMR channels without repositioning the catheter. Providing a catheter made of a superelastic material to avoid the heating or electrical requirements of shape memory materials would be particularly desirable.

ADVANTAGES AND SUMMARY OF THE INVENTION

Thus, it is an advantage of the present invention to provide a catheter apparatus and method of use for percutaneous and other intra-vascular procedures, including TMR, or any stimulation procedure, which overcome the limitations of the prior art.

It is a further advantage of the present invention to provide a catheter apparatus capable of being guided into a heart chamber and used therein for creating a plurality of TMR channels controllably and efficiently.

It is a further advantage of the present invention to provide a catheter made, at least in part, of a superelastic material or a shape memory material having a preformed operative shape, which, to facilitate insertion into the patent and through or into at least a portion of the vasculature or other body lumen or opening, can be temporarily deformed, such that upon positioning adjacent a selected surface, the catheter will or can be returned to the preformed operative shape.

It is a further advantage of the present invention to provide a bow shaped catheter apparatus with an integrated guide wire and defining a bow shaped shaft with a number of guide holes at its distal end. The catheter apparatus has at least one lumen extending therethrough, or at least partially therethrough, for selectively directing the distal end of an optical fiber, other type of laser delivery means or other device through the guide holes on the shaped shaft.

It is yet a further advantage of the present invention to provide a percutaneous catheter which can be positioned securely into a selected position within the ventricle.

A further advantage of the present invention is to provide an apparatus to enable creation of a plurality of appropriately grouped and spaced TMR channels on a selected surface within a body cavity or organ quickly and safely, without the need for repositioning the catheter before creation of each successive hole.

Therefore, to summarize the present invention, a bow shaped shaft with more than one guide hole at its distal end, and at least one lumen therein for selectively directing the distal end of an optical fiber, other type of laser delivery means or other device through the guide holes on the shaped shaft, particularly adapted for percutaneous TMR, is disclosed herein. The catheter apparatus is comprised essentially of an outer shaft having a generally bow shaped distal end, thus defining an outer arcuate sidewall portion and an inner arcuate sidewall portion of the generally bow shaped distal end. The shaft has a plurality of guide holes located at selected positions adjacent to the distal end of the shaft, communicating with the at least one lumen. The catheter apparatus can be made at least partially of superelastic and/or shape memory materials of construction.

The shaft is designed to be placed adjacent selected portions of tissue, such as within the left ventricle, and is somewhat flexible. Thus, a laser delivery means such as an optical fiber or fiber bundle, or other functional device, can be extended through the lumen of the shaft for exit through any one of the guide holes on the shaft. The flexible, shaped curvature of the distal end of the shaft allows the distal end of the laser delivery means to be extended through the guide holes of the shaft in contact with the selected surface structure for treatment thereon. Thus, with regard to TMR, a laser delivery means, such as an optical fiber or fiber bundle, can be advanced through the guide holes for creating a series of TMR channels. Furthermore, with regard to non-laser TMR, a cannula or trocar assembly may be extended into the tissue of the left ventricle, with or without use of a mechanical piercing tool.

Numerous other advantages and features of the present invention will become readily apparent from the following detailed description of the invention and the embodiments thereof, from the claims and from the accompanying drawings.

DETAILED DESCRIPTION OF THE PREFERRED EMBODIMENT

Preferred Apparatus

Figure 1:
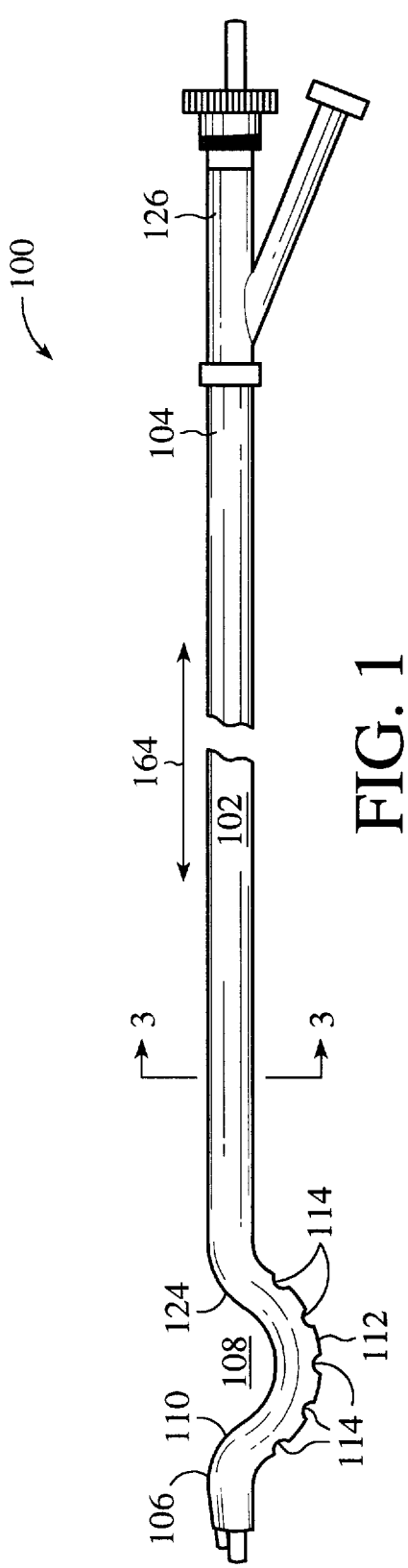
FIG. 1 is a representative isometric view of a preferred embodiment of the bow shaped catheter of the present invention.
Figure 2:
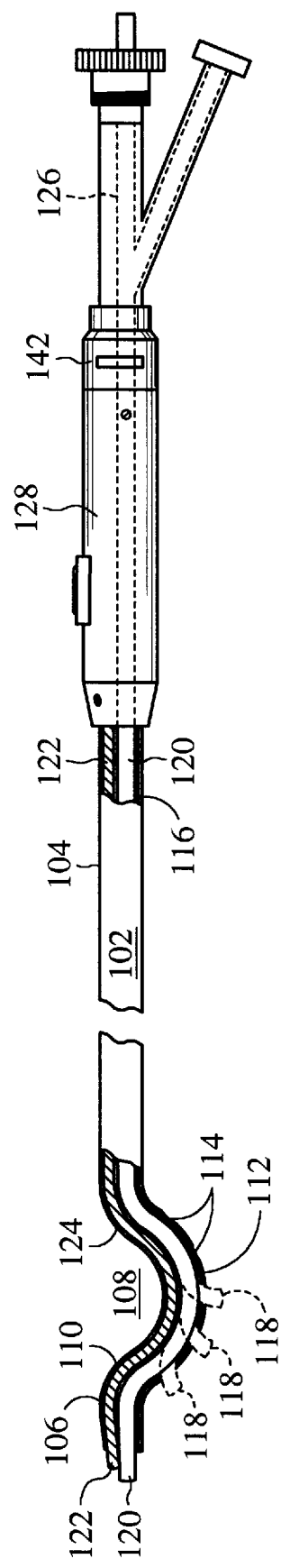
FIG. 2 is a representative section view of a preferred embodiment of the bow shaped catheter of the present invention.
Figure 3:
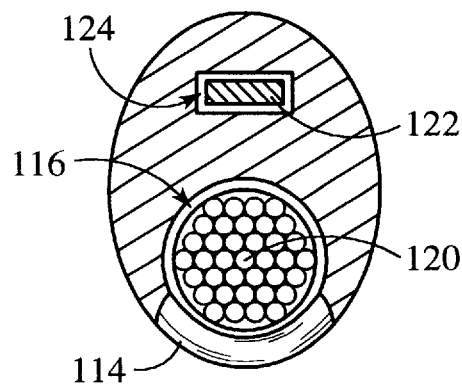
FIG. 3 is a representative section view of a preferred embodiment of the bow shaped catheter of the present invention taken at 3—3.

FIG. 1 is a representative isometric view of a preferred embodiment of the bow shaped catheter 100 of the present invention. FIG. 2 is a representative section view of a preferred embodiment of the bow shaped catheter 100 of the present invention. FIG. 3 is a representative section view of a preferred embodiment of the bow shaped catheter of the present invention taken at 3—3.

With reference to the figures, a main catheter shaft 102 has both a proximal end 104 and a distal end 106. A bow shaped portion 108 near the distal end 106 defines an inner arcuate sidewall 110 and an outer arcuate sidewall 112. A plurality of individual guide holes 114 are disposed on at least the outer arcuate sidewall 112 of the bowed portion 108 of the main catheter shaft 102. The plurality of guide holes 114 communicate with a laser delivery means or other functional device lumen 116 which extends through the shaft 102. Thus, the distal end 118 of an optical fiber, fiber bundle or other laser delivery means 120 inserted into the laser delivery means or other functional device lumen 116 at the proximal end 104 of the catheter shaft 102 can selectively engage and advance through the plurality of guide holes 114 as desired. The guide holes 114 must be formed in the outer shaft 102 in such a way as to permit steerability of the distal end 118 of laser delivery means 120 therethrough. Typically, these guide holes will be elongated into an oval or ellipse shape, although they may define other shapes, such as rectangles. They will be smoothed, rounded or otherwise treated to facilitate and enhance the exit of the laser delivery means 120. In a preferred embodiment, generally from 1–6 holes can be created, spaced approximately 0.5–2 centimeters or so apart, and it will be understood that spacing will be related to the procedure to be performed.

Figure 8:
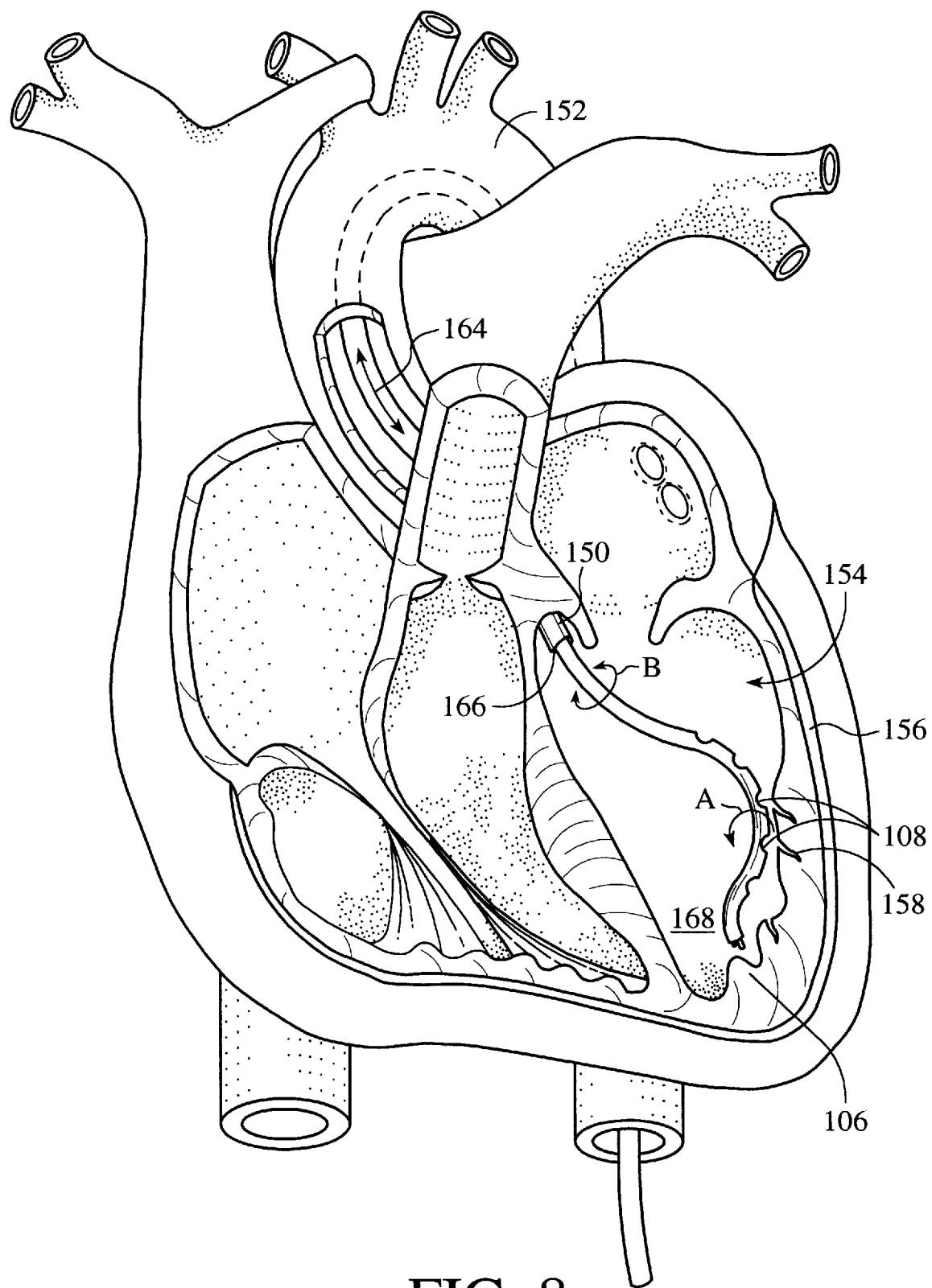
FIG. 8 is a representative perspective view of a preferred embodiment of a bow shaped catheter of the present invention positioned inside the left ventricle of the heart in a first position.

As shown best in FIGS. 2 and 3, an integrated wire 122 extends through a second lumen 124 in shaft 102. The integrated wire 122 terminates at or adjacent the distal end 106 of shaft 102. The integrated wire 122 is preferably made at least partially of, or otherwise comprises, a superelastic material which can be given a selected shape. Other suitable materials include spring steel, stainless steel, shape memory or superelastic/shape memory alloys. Once the superelastic material has been shaped, it can be said to have "memorized" the shape. It is flexible enough to be pushed and steered through bends and turns along desired paths within the body, typically with the use of a guide catheter which will help straighten out the bowed portion or other preformed, memory curvature in the catheter. In TMR, application of laser energy to portions of endocardium 156 from within the left ventricular chamber of the heart can be achieved, for example, by introducing the catheter 100 via the femoral artery, through the aorta, over the aortic arch 152 and into the left ventricle 154 as shown in FIG. 8. This can also be done with the use of a guide catheter 150 or other outer sheath to aid in the straightening of the bow shaped portion 108.

As shown in FIGS. 1–3, it will be apparent that while the integrated wire 122 can be rigidly fixed in place within the second lumen 124, it can also be slidably disposed within the lumen. Furthermore, the integrated wire 122 can be replaced with another completely different means for causing the distal end 106 of the catheter shaft 102 to have a bow shaped portion 108. Thus the integrated wire apparatus can also be manufactured as an over-the-wire design catheter, in which case the free sliding wire would have a preshaped bow shape portion. Furthermore, manufacturing the entire main catheter shaft 102 or just the bow shaped portion 108 out of superelastic or shape memory material, as described herein, could eliminate the need for an integrated wire, slidable or not, altogether.

Upon deformation of the shaped material at temperatures somewhat below the transition temperature, forces developed in the material will tend to return it to the preformed shape with spring-like action upon release of restraining forces. Thus, the bow shaped portion 108 of the main catheter shaft 102 can be temporarily deformed (substantially straightened) and positioned inside the left ventricle 154 or other body opening by passing it through a guide catheter 150 through the vasculature in an essentially elongated shape. The main catheter shaft 102 is also flexible enough to be pushed and steered through bends and turns along desired paths within the body. For example, catheterization procedures often involve introducing such equipment to the human body via the femoral artery and advancing the equipment to the desired location through the vasculature. Then, once inside the ventricle, other heart chamber or other opening large enough, the superelastic material in the bow shaped portion 108 will act like a spring and retract in length while assuming the preformed shape. Finally, the bow shaped portion 108 will be springy enough, if and when retracted back into a guide catheter or other outer lumen, to be temporarily deformed again.

In the case of shape memory materials, a "memory" or preformed shape can be given to the main catheter shaft, the integrated guide wire, etc. Then, the percutaneous apparatus can be deformed temporarily and extended through the vasculature, without internal stress. Once the distal end 106 of the main catheter shaft 102 is in position, the preformed operative shape (such as the bow shape) can be reproduced by any of different ways. These include heating using electrical resistance, radio frequencies, microwaves, circulating heated fluid, etc. It will also be understood that the integrated wire could also be a type of "hypo" tube, i.e. an additional tube inside a lumen for introduction of fluids, other tools, etc. Furthermore, by providing distinctive cross section geometries, the components can be "keyed" together as desired. For example, in a preferred embodiment, the slidable wire 122 and the second lumen 124 are keyed together to prevent undesired rotation of one or the other component, as well as to provide rotational control to the physician, as shown in FIG. 3.

A wye or other coupling means 126 provides a means for introducing other equipment such as tools or probes for visualization or other recording or monitoring functions, flushing or cleaning, drugs or other materials into the catheter 100. Optionally, a handle means 128 can be provided at the proximal end 104 of the shaft 102. Thus, an optical fiber, bundle or other laser delivery means 120 can be controllably advanced and retracted through the laser delivery means or other functional device lumen 116 by manipulating the handle means 128. It will be understood that the handle means 128 may act with the wye coupling means 126 adapted for allowing fluid flow through the proximal end 132 of handle means 128, or the handle means 128 or the wye coupling means may be used alone.

Figure 4:
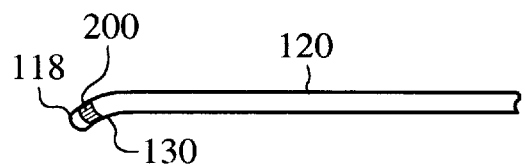
FIG. 4 is a is a representative view of the distal end of a laser delivery means for use with a preferred embodiment of the bow shaped catheter of the present invention.

FIG. 4 is a is a representative view of the distal end 118 of a laser delivery means 120 for use with a preferred embodiment of the bow shaped catheter of the present invention. The distal end 118 of the laser delivery means 120 optionally is provided with a slight deflection or curvature 130. As will be understood, this curvature 130 will assist the physician in controllably engaging and extending the distal end 118 of the laser delivery means 120 sequentially through the individual guide holes 114. It will be understood that the slight curvature 130 of the distal end 118 of laser delivery means 120 can be made in any of several different ways, including a permanent curvature of an outer tubing cover formed by heat, molding, laminated construction, etc., or a temporary curvature formed by a wire or shim construction, super elastic or shape memory material of construction, etc. Radiopaque marker 200 such as a band of platinum will provide and improve visualization of the apparatus and associated procedure. Visualization of such marker 200 will permit the physician to locate the distal tip 118 of laser delivery means 120 conveniently and precisely.

Figure 5:
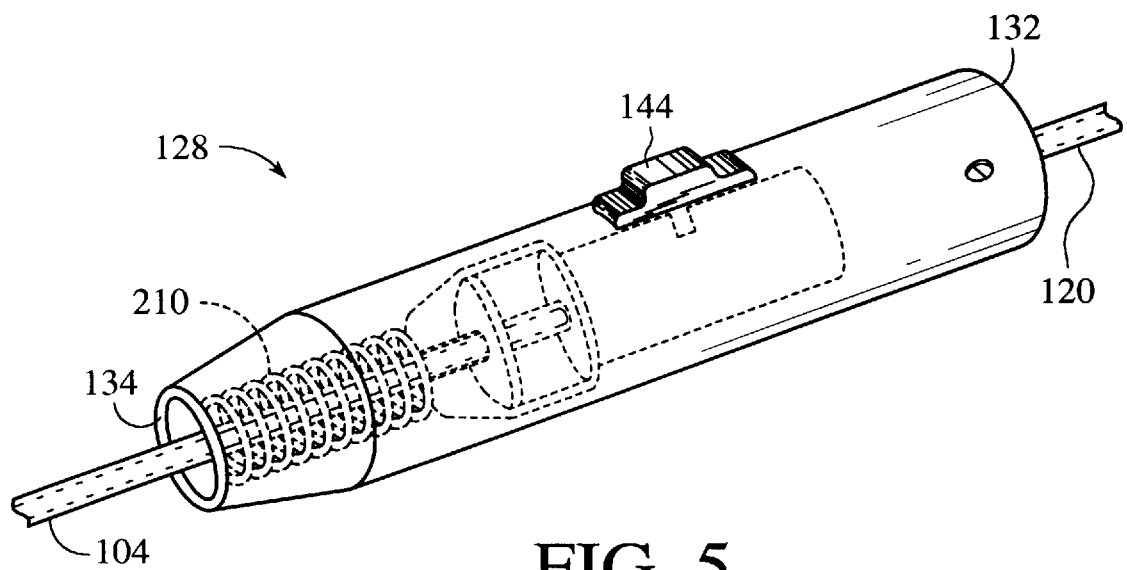
FIG. 5 is a representative isometric view of a preferred embodiment of a handle means of a bow shaped catheter of the present invention.
Figure 6:
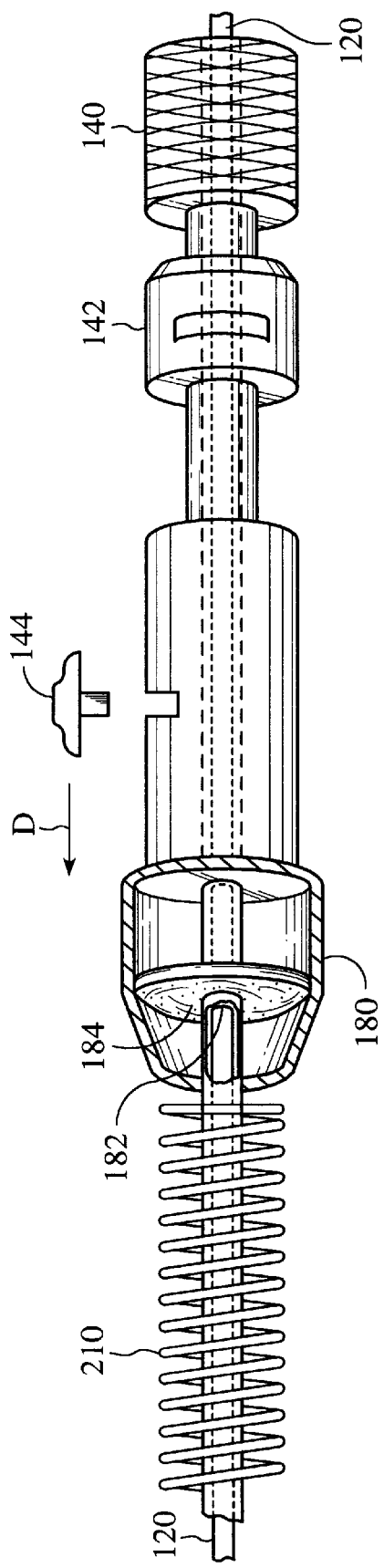
FIG. 6 is a representative view showing the internal assembly of a preferred embodiment of the handle means of a bow shaped catheter of the present invention.

FIG. 5 is a representative isometric view of a preferred embodiment of a handle means 128 of a bow shaped catheter of the present invention and FIG. 6 is a representative view showing the internal assembly of a preferred embodiment of the handle means 128 of the bow shaped catheter of the present invention. The handle means has both a proximal end 132 and a distal end 134. Internal to handle means 128 is blood seal assembly. In the preferred embodiment, laser delivery means 120 or other functional device passes through a diaphragm member 180, consisting essentially of a small hole or aperture 182 in a flexible polymeric portion 184. Thus, a fluid seal is created by flexible portion 184 squeezed around tubular laser delivery means 120.

Adjacent the coupling means 140, depth stop bushing 142 will limit the travel of the laser delivery means 120 through the catheter assembly. Slider knob 144 mounted through slot 146 onto coupling means 140 provides a manual fiber feed mechanism. It will be understood by those skilled in the art that other laser delivery means advance mechanisms can be used with the catheter assembly 100 of the present invention. Thus, slider knob 144 mounted within slot 146 will controllably advance and retract the laser delivery means 120 through the laser delivery means or other functional device lumen 116 in the main catheter shaft 102. It will be understood, and therefore included within the scope of this invention, that the manually operated linkage laser delivery means advance mechanism can be replaced with a wide range of different mechanisms or devices, including indexed or ratcheted mechanisms, electric drives with electronic controllers, etc.

At the proximal end 132 of the handle means 128 there is a laser delivery means coupling means 140 such as a Thuoy-Borst type crimp clamp connector, etc. Other such fiber and fiber bundle coupling means 140 are included in the scope of the present invention.

Figure 7:
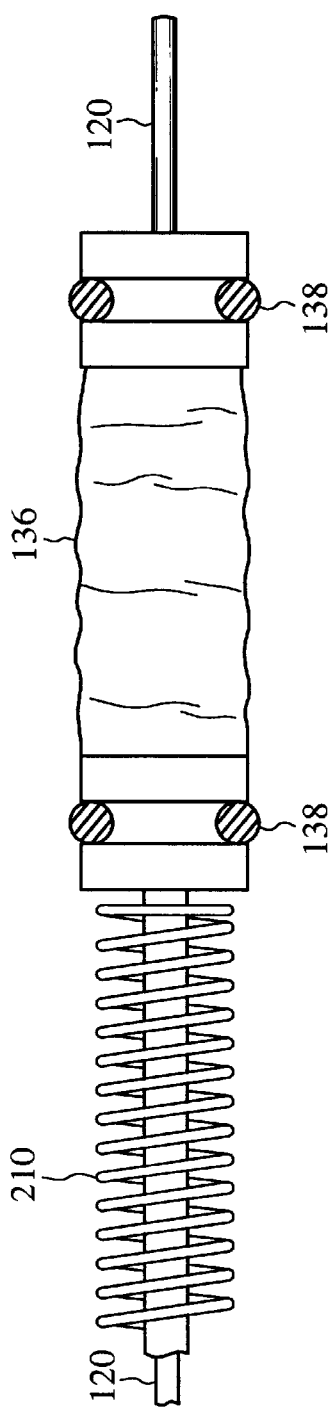
FIG. 7 is a representative detail view of another preferred embodiment of a blood seal internal to the handle means of the present invention.

FIG. 7 is a representative detail view of another preferred embodiment of a blood seal means. The apparatus comprises a collapsible piece of tubing 136 with sealing means 138 such as O-rings at either end.

It will be understood that biasing means 210 such as a coil or other type spring, as shown in FIGS. 5–7, will be placed inside handle means 128 such that the fiber advance mechanism biases the laser delivery means 120 into a fully retracted position.

FIG. 8 is a representative perspective view of a preferred embodiment of the bow shaped catheter 100 of the present invention positioned inside the left ventricle 154 of the heart in a first position A. As an "access-assisted system", a guide catheter 150 is introduced over the aortic arch 152 and through the aortic valve into the left ventricle 154. The use and apparatus of such guide catheters 150 is included within the scope of the present invention. The bow shaped catheter 100 can be guided through the guide catheter 150 into a first position A with distal end 106 seated within the apex 168 of the left ventricle 154 or other opening. The apex-seeking distal end 106 is stabilized by the apex 168 such that during laser delivery or other treatment with laser delivery means 120 or other functional device, as well as during retraction of the laser delivery means 120, the position is maintained and TMR channels or other treatment can be performed with the laser delivery means or other functional device alternatingly extended and retracted through guide holes 114 at precisely-spaced intervals in accurate alignment, as desired. This position A is adjacent a first surface area 156, in this case a portion of endocardium 156 in the left ventricle 154. In this position, the catheter can treat a series of individual selected treatment points 158 of endocardium 156. Such treatment points 158 would typically be TMR channels or stimulation sites. Following treatment, the apparatus 100 can be rotated in the direction shown by directional arrow B. This would result in placing the catheter 100 in another position. One or more additional series of individual selected treatment points on endocardium 156 can also be treated. It will be clear that the apparatus of the present invention can be rotated about apparatus 100 central axis 164 through a wide range of angular positions so as to treat many different surface areas during a given procedure. As indicated above, a key feature of the present invention is the ability to stabilize the distal end 106 in the apex 168 of the left ventricle 154 to provide a stable, positioned catheter for treating at a plurality of sites conveniently and controllably. Furthermore, compressing the bow shaped portion 108 by continued advance of the apparatus will assist the physician maintain contact between the operative, curved portion 108 and the heart wall or other surface area 156, especially in larger chambers or openings. Furthermore, it will be understood by the disclosure herein that the need to provide guide catheter 150 when the guide wire, lumens or other components of the catheter assembly are constructed of shape memory materials.

Figure 9:
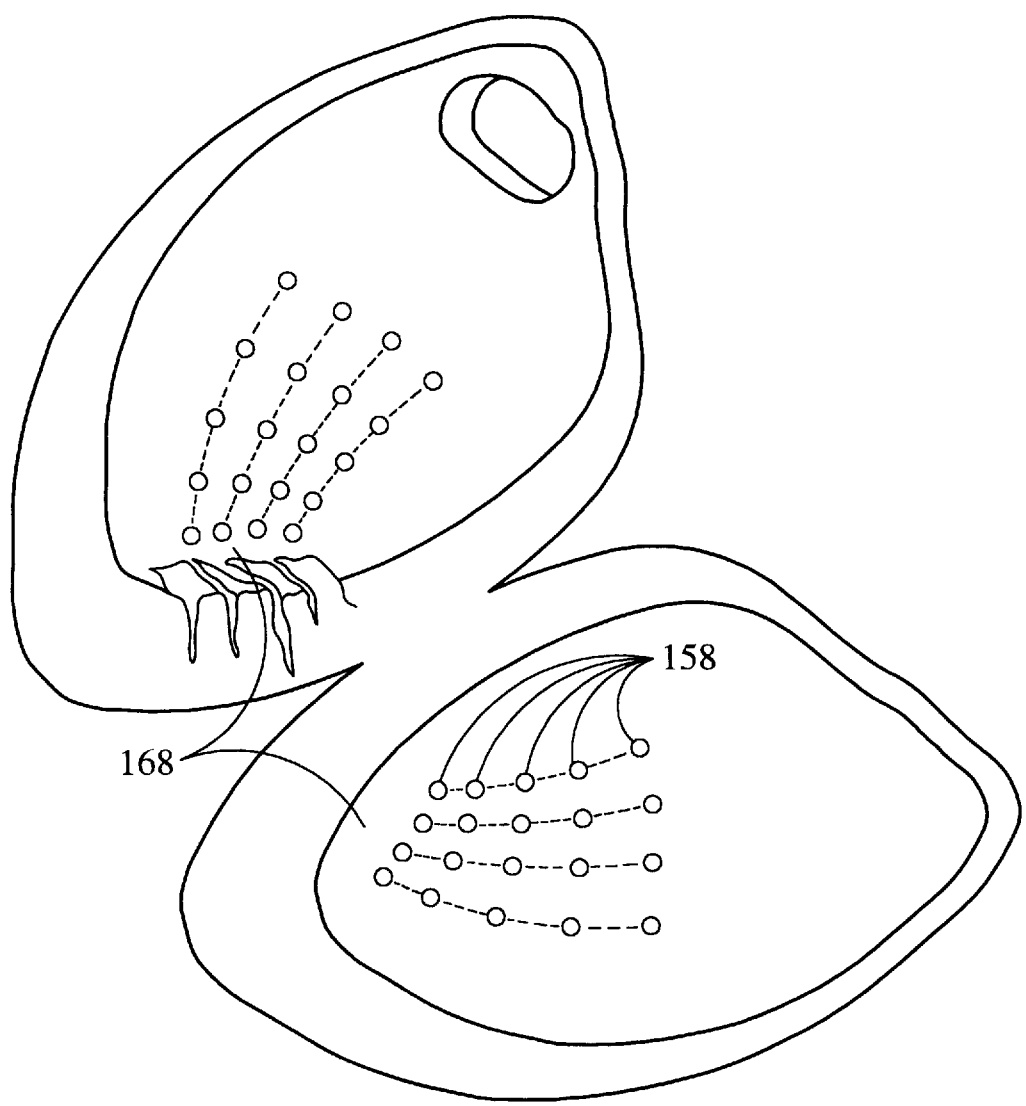
FIG. 9 is a representative perspective view of a treatment pattern made by a preferred embodiment of a bow shaped catheter of the present invention.

FIG. 9 is a representative perspective view of a treatment pattern made by a preferred embodiment of a bow shaped catheter 100 of the present invention. This view is of the inside portion of the left ventricle 154. As described above, in the case of TMR, a first set of individual TMR channels 158 in a single row can be created by alternatingly extending and retracting laser delivery means 120 sequentially through the plurality of guide holes 114 of the main catheter shaft 102. Thereafter, by precisely controlled rotation of the apparatus about its central axis 164, as shown in the prior figure, additional rows or sets of individual TMR channels can also be created essentially parallel to the first set of individual TMR channels 158, to effectively cover a significant portion of interior heart wall as desired.

It will be understood that essentially any desired number or density of TMR channels can be created in a given portion of the heart. Thermal energy accumulation as well as interconnection of adjacent channels are factors, among others, to be considered in such dense TMR channeling schemes. Saline flushing and/or cooling may also be indicated in certain circumstances.

Preferred Method

As indicated above with regard to FIGS. 1–9, the present invention is directed generally to "access-assisted systems", i.e. to catheter systems which are guided into and through parts of the body, such as into the left ventricle 154, by use of a guide catheter 150 or other guide system. Such guide catheters are well known and included within the scope of this invention. Typically, entry into the vasculature is made through the femoral artery. The physician steers the guide catheter 150 over the aortic arch 152 and across the aortic valve.

In a preferred embodiment, initial preparation of catheter 100 includes extension of laser delivery means 120 fully through the main catheter shaft 102 so as to position the distal end 118 of laser delivery means 120 substantially at or adjacent the distal end 106 of the shaft 102. In this manner, it is possible to extend the catheter 100 with the bow shaped portion 108 temporarily deformed and elongated within a guide catheter 150, through the vasculature and steer it into the left ventricle 154. Once the bow shaped portion 108 is extended past the distal end 166 of guide catheter 150 inside the left ventricle, the guide catheter 150 can be retracted as desired.

Once inside the left ventricle 154, the bow shaped outer shaft 102 will be allowed to assume its operative bow shape and will be positionable against a curved wall structure in a first position or orientation A with the apex-seeking distal end 106 of the main catheter shaft 102 securely, but not traumatically, stabilized and seated within the apex 168 of the left ventricle 154. At this point in the procedure, a first TMR channel 158 or other laser treated site can be created by controllably advancing the distal end 118 of laser delivery means 120 through the first guide hole 114, i.e. the guide hole 114 most distal on shaft 102, such as by manually or otherwise urging slider 144 in a forward direction D toward the distal end 134 of handle means 128. As disclosed, in the case of TMR, the laser delivery means 120 could be an optical fiber or fiber bundle which would be extended through the laser delivery means or other functional device lumen 116 of catheter shaft 102 into an endocardial surface 156 for the creation of channels into myocardium.

As the laser delivery means 120 is advanced, blood seal means will prevent the backflow of blood from the left ventricle 154 through shaft 102 and out the proximal end 132 of handle means 128. In a preferred embodiment, the actual length of slot 146 will determine the length of travel of the distal end 118 of laser delivery means 120 into myocardium. In the event no handle is used with the catheter assembly 100, it will be understood that any backflow preventer, check valve, blood seal, etc. with the necessary operative function and suitability can be employed at a proximal end 106 of the main shaft 102 and will be included within the scope of the present invention.

It will be understood that visualization enhancement aids, including but not limited to radio-opaque markers, and/or platinum bands, foils, strips or other on the various components of the present invention, including on the main catheter shaft 102, at the distal end 106, on the bowed portion 108, at or near individual guide holes 114, or at any position on the laser delivery means 120, optical fiber or fiber bundle, or other functional device, will be very helpful in visualization of the percutaneous procedure.

It will be understood that by providing a piercing tip or other piercing means in conjunction with the distal end 118 of laser delivery means 120, the catheter 100 can also be used initially to pierce endocardial or other selected surface 156. Such piercing or mechanical cutting device includes, but is not limited to the following: curved or flat cutting blades, hollow piercing needles, retractable, flaring, anchoring or clamping tips, and the like. The piercing tip may be any fiber bundle, or may be a sharpened fiber or fiber bundle as disclosed in U.S. Pat. No. 5,703,985 incorporated herein by reference. Immediately following initial piercing which anchors the tip of the fiber to the wall of the ventricle, advancing laser delivery means 120 a selected distance into the myocardium while simultaneously delivering laser energy will create a TMR channel or other treatment site. Alternatively, retro-lasing may be performed. This novel method includes the steps of advancing laser delivery means 120 with a piercing tip a selected distance into the myocardium and then delivering laser energy to create a TMR channel or other treatment site while simultaneously retracting the fiber, laser delivery means 120 or other functional device to create the channel as the distal end 118 of laser delivery means 120 is being retracted through myocardium. With this procedure, with regard to TMR especially, inasmuch as laser energy is only delivered during retraction of the fiber, the possibility of advancing the fiber too far and lasing through the epicardium is eliminated, the risks of complications arising from such epicardial perforations, including but not limited to cardiac tamponade (a buildup of pressure in the pericardial sac caused by the presence of an excess of fluid such as blood), proliferation of adhesions between the epicardium and the pericardial sac (thereby preventing normal, frictionless enclosure of the heart muscle within the pericardial sac), etc. are minimized.

Once a first TMR channel 158 or other laser treated site is created, slider 144 can be repositioned, such as by biasing recoil spring 210, so as to retract the distal end 118 of laser delivery means 120 into shaft 102. Slight further retraction will engage the distal end 118 of laser delivery means 120 with the second guide hole 114 closest to the distal end 106 of shaft 102. As disclosed, a slight deflection or curvature 130 located at or adjacent the distal end 118 of laser delivery means 120 will assist the physician in controllably selecting and engaging any one of the plurality of guide holes 114 on the bow shaped portion 108 of shaft 102. It will be understood, however, as disclosed above, that sequential advance, retraction and engagement of a guide hole 114 is most efficiently performed at sequential, successive guide holes 114, and that therefore, while in a first position or orientation A within the left ventricle 154, a series of TMR channels 158 will be created with the first channel made in, at or near the apex 168 of the left ventricle 154, and with successive channels created in essentially and substantially a straight line ascending the endocardial surface 156 from bottom to top.

Additionally, rotation of the catheter apparatus about its central axis 164 will allow the apparatus to be repositioned into a second position such that it can be placed adjacent additional surfaces or structures for treatment thereon or therein. It will be understood that prior to rotation, laser delivery means 120 should be retracted at least such that distal end 118 is within shaft 102 to prevent injury to an endocardial surface. At this point, laser delivery means can be fully extended into the shaft such that distal end 118 of laser delivery means 120 is within the shaft adjacent the distal end 106 of shaft 102 adjacent the distal most guide hole 114. Then, once slight rotation of catheter 100 about axis 164 is accomplished, the steps of advancing laser delivery means 120 out the first guide hole 114, creation of a TMR channel or other laser treated site, retraction of the distal end 118 of laser delivery means 120 into shaft 102 and engaging the second or next successive guide hole 114 for advance therethrough can be repeated for each guide hole 114 on the bow shaped portion 108, as desired. By repeating the sequence, an entire TMR procedure placing a large number of appropriately grouped and spaced TMR channels from one or more endocardial surfaces can be accomplished rapidly and uniformly.

Furthermore, adjunct use of appropriate drug delivery apparatus, blood scale means, depth stop apparatus such as clamps, etc., visualization means, marker means as well as other hardware and methodology will be considered within the scope of the present invention. Visualization can be enhanced with ultrasound for precise and accurate positioning of the apparatus. Additionally, use of electro physiology (EP) for confirming tissue contact will be particularly useful.

The present invention is intended for use with any medical laser. In particular, the Holmium or excimer laser is particularly suited to the present invention. However, any suitable laser source, pulsed or otherwise, could provide laser energy to the laser delivery means of the present invention for performing the method of the present invention. Likewise, the catheter and surgical equipment, including laser delivery means, referred to in the present document as well as that known and used in medicine and other disciplines today and in the future, will be included in the scope of this disclosure. Such laser delivery means include, but are not limited to, individual optical fibers as well as bundles of fibers with and without piercing tips and with or without firing tips or fiber ends having shaped or contoured end faces for selectively diverging the laser beam or other laser energy diverging means, rods, mirrors configurations and other laser delivery means with and without focusing lens and the like. It will also be understood that the apparatus and method of the present invention as described herein including the novel combination or use with any conventional mechanism or method which are known to those skilled in the art, are included within the scope of this invention. Furthermore, with regard to non-laser TMR, a cannula or trocar assembly may be extended into the tissue of the left ventricle, with or without use of a mechanical piercing tool.

It will further be understood that while the present invention has been described for performing TMR on endocardial surfaces in the left ventricle, the apparatus and methods described herein are equally intended for use in any suitable procedure, including but not limited to procedures where any device need be extended through a guide catheter to an opening or other point within the body for other medical procedures including laser treatment, visualization, biopsy, etc. "Stimulation", for example, is performed by using laser energy to create zones or pockets, optionally interconnected at least initially by small channels ablated through the tissue, for the introduction of blood born growth and healing factors and stimulated capillary growth surrounding the lased zones or pockets to create an increased supply of oxygen to the tissue and thus a revitalization of the heart muscle. Methods and apparatus for causing stimulation are more fully described in co-pending U.S. patent application Ser. No. 08/664,956, allowed, filed Jun. 13, 1996.

While the principles of the invention have been made clear in illustrative embodiments, there will be immediately obvious to those skilled in the art many modifications of structure, arrangement, proportions, the elements, materials, and components used in the practice of the invention, and otherwise, which are particularly adapted to specific environments and operative requirements without departing from those principles. The appended claims are intended to cover and embrace any and all such modifications, with the limits only of the true spirit and scope of the invention.

I claim:

1. A catheter device for an interventional procedure within a body cavity by passage through vasculature, the device comprising:
   a) a flexible shaft having a proximal end, a distal end and at least a first and second axially extending there through;
   b) an interventional procedural device for performing an interventional procedure to a selected surface within the body cavity, having proximal and distal ends, and housed in and advanceable through the first lumen in the flexible shaft;
   c) a flexible wire disposed within the second lumen of the flexible shaft, the flexible wire causing the distal end of the flexible shaft to change from a substantially elongated shape during passage within the vasculature into a bow shaped portion within the body cavity; and
   d) a plurality of guide holes disposed on at least the bowed shaped portion of the flexible shaft and in communication with the first lumen of the flexible shaft, wherein the interventional procedural device selectively extends through any of the guide holes,
   whereby the bow shaped portion of the flexible shaft facilitates positioning of the catheter device for creation of an interventional treatment pattern and stability of the catheter device within the body cavity.

2. The device of claim 1 wherein the interventional procedural device is a laser energy delivery device.

3. The device of claim 2 further comprising a handle member including a device for controllably advancing a distal end of the laser energy delivery device.

4. The device of claim 2 wherein the laser energy delivery device includes a depth stop member for limiting displacement of the laser energy delivery device.

5. The device of claim 2 wherein the laser energy delivery device includes a fluid seal member for preventing fluid flow through the first lumen.

6. The device of claim 2 wherein the laser energy delivery device comprises at least one optical fiber.

7. The device of claim 2 wherein the distal end of the laser energy delivery device includes a focusing device whereby the laser delivery device emits laser energy and the focusing device is for diverging the laser energy emitted.

8. The device of claim 2 wherein the laser delivery device has a distal end with curvature, whereby the curvature assists advancement of the laser energy delivery device through any one of the guide holes.

9. The device of claim 1 wherein the wire has a non-circular cross-sectional shape keyed to the cross-sectional shape of the second lumen thereby preventing wire rotation.

10. The device of claim 1 wherein the wire is at least partially comprised of a material selected from the group consisting of superelastic, shape memory alloy and stainless steel.

11. The device of claim 1 wherein the wire is rigidly fixed in place in the second lumen of the flexible shaft.

12. The device of claim 1 wherein the wire is slidably disposed within the second lumen of the flexible shaft.

13. The device of claim 1 wherein the wire is comprised of material selected from the group consisting of superelastic and shape memory alloy material.

14. The device of claim 1 wherein the interventional procedural device includes a device for controllably advancing a distal end of the interventional procedural device.

15. The device of claim 1 wherein the interventional procedural device comprises a visualizing enhancement device.

16. A method for performing an interventional procedure in a body cavity, the method comprising:
   a) providing a catheter device having proximal and distal ends comprising a flexible shaft portion at the distal end, the flexible shaft portion having a proximal end, a distal end and at least a first and second axially extending there through, an interventional procedural device for performing an interventional procedure housed in and advanceable through the first lumen in the flexible shaft, a flexible wire disposed within the second lumen of the flexible shaft, the flexible wire causing the distal end of the flexible shaft to change from a substantially elongated shape during passage within the vasculature into a bow shaped portion within the body cavity, and a plurality of guide holes disposed on at least the bowed shaped portion of the flexible shaft and in communication with the first lumen of the flexible shaft;
   b) advancing the distal end of the flexible shaft through the vasculature in a generally elongated shaped form into the body cavity;
   c) causing the distal end of the flexible shaft to change into a bow shape and positioning the bow shaped portion of the flexible shaft adjacent a selected surface within the body cavity;
   d) extending the interventional procedural device through one of the guide holes disposed in the bow shaped portion of the flexible shaft; and
   e) treating a selected surface within the body cavity.

17. The method of claim 16 further including the step of:
f) creating an interventional treatment pattern within the body cavity.

18. The method of claim 16 wherein step b) further includes deploying a guide catheter through the vasculature and advancing the flexible shaft through the guide catheter for positioning in the body cavity.

19. The method of claim 16 further including the steps of:
f) retracting the distal end of the interventional procedural device through the guide hole into the distal end of the flexible shaft;
g) repositioning the distal end of the interventional procedural device adjacent a second guide hole;
h) extending the distal end of the interventional procedural device through the second guide hole; and
i) treating the selected surface within the body cavity.

20. The method of claim 16 further including the steps of:
f) retracting the distal end of the interventional procedural device through the guide hole into the distal end of the flexible shaft;
g) rotating the bow shaped portion of the flexible shaft within the body cavity to position the device adjacent an additional selected surface within the body cavity;
h) re-extending the interventional procedural device through one of the guide holes; and
i) treating the additional selected surface within the body cavity.

21. The method of claim 16 wherein the selected surface within the body cavity is an endocardial surface in a heart.

22. The method of claim 16 wherein the interventional procedure is myocardial revascularization.

23. The method of claim 16 wherein the interventional procedure is myocardial revascularization, the interventional procedural device is a laser delivery device and the selected surface is an endocardial surface within a heart and step e) includes treating from the endocardial surface by delivering channel forming energy from the laser delivery device thereby creating a revascularizing channel into myocardium.

24. The method of claim 23 wherein step e) is preceded by the step of piercing the endocardial surface by the interventional procedural device.

25. The method of claim 23 wherein the interventional procedure further includes stimulation and step e) further includes creating stimulation voids within the myocardium.

26. The method of claim 16 wherein the body cavity is a ventricle of a heart and step c) includes positioning the distal end of the flexible shaft at an apex of the heart ventricle.

27. The method of claim 16 wherein the interventional procedure is stimulation, the interventional procedural device is a laser delivery device and step e) includes creating voids within myocardial tissue.

* * * * *